United States Patent [19]
Russell

[11] Patent Number: 5,656,158
[45] Date of Patent: Aug. 12, 1997

[54] PROCESS FOR THE PREPARATION OF CELLULOSE BASED CHIRAL SEPARATION LIQUID CHROMATOGRAPHY STATIONARY PHASE

[75] Inventor: John W. Russell, Midland, Mich.

[73] Assignee: The Dow Chemical Company, Midland, Mich.

[21] Appl. No.: 715,660

[22] Filed: Sep. 18, 1996

Related U.S. Application Data

[62] Division of Ser. No. 402,663, Mar. 13, 1995, Pat. No. 5,589,061.

[51] Int. Cl.$^6$ ................................................. B01D 15/08
[52] U.S. Cl. .................... 210/198.2; 210/635; 210/656; 210/502.1; 502/404; 502/439; 536/56
[58] Field of Search ................................ 210/635, 656, 210/657, 658, 659, 198.2, 198.3, 502.1; 502/401, 404, 439; 536/56

[56] References Cited

U.S. PATENT DOCUMENTS

| | | | |
|---|---|---|---|
| 3,950,282 | 4/1976 | Gilbert | 536/32 |
| 4,131,727 | 12/1978 | Lange | 536/112 |
| 4,786,416 | 11/1988 | Yuki | 210/198.2 |
| 4,818,394 | 4/1989 | Okamoto | 210/198.2 |
| 4,879,038 | 11/1989 | Namikoshi | 210/198.2 |
| 4,892,659 | 1/1990 | Shibata | 210/198.2 |
| 4,931,184 | 6/1990 | Okamoto | 210/198.2 |
| 5,026,841 | 6/1991 | Francotte | 536/58 |
| 5,091,520 | 2/1992 | Francotte | 536/56 |

OTHER PUBLICATIONS

"For Superior Chiral Separation Chiral HPLC Column", *Chiral Technologies, Inc.*, pp. 1 and 2, undated.

Hesse, G., et al. "Eine vollständige Racemattrennung durch Elutions–Chromatographie an Cellulose–triacetat", *Chromatographia*, vol. 6, No.6 Jun. (1973) pp. 277–280 & 4 pages of translation.

Okamoto, Y., et al., "Cellulose Tribenzoate Derivatives As Chiral Stationary Phases for High–Performance Liquid Chromatography" *Journal of Chromatography*, 389 (1987) pp. 95–102.

Ichida A., "Resolution of Enantiomers by HPLC on Cellulose Derivatives", *Chromatographia*, vol. 19, pp. 280–284, 1985.

Francotte, E., et al. "Benzoyl Cellulose Beads in the Pure Polymeric Form as a New Powerful Sorbent for the Chromatographic Resolution of Racemates", *Chirality*, 3:43–55 (1991) pp. 43–55.

Francotte, E., et al. "Chromatographic resolution on methylbenzoylcellulose beads" *Journal of Chromatography*, 595 (1992) pp. 63–75.

*Primary Examiner*—Ernest G. Therkorn
*Attorney, Agent, or Firm*—Timothy S. Stevens

[57] ABSTRACT

A process for preparing a cellulose ester liquid chromatographic stationary phase by reacting cellulose with an aromatic acid halide, such as p-toluoyl chloride, in the presence of a base catalyst, such as pyridine, the reaction temperature and the concentration of base catalyst being below the temperature and concentration at which the cellulose ester dissolves, the reaction time being less than the reaction time at which the cellulose ester dissolves. Similarly, a process for preparing a cellulose carbamate liquid chromatographic stationary phase by reacting cellulose with an aromatic isocyanate, such as 3,5-dimethyl phenyl isocyanate, in the presence of a base catalyst, such as pyridine, the reaction temperature and the concentration of base catalyst being below the temperature and concentration at which the cellulose carbamate dissolves, the reaction time being less than the reaction time at which the cellulose carbamate dissolves.

15 Claims, 1 Drawing Sheet

PROCESS FOR THE PREPARATION OF CELLULOSE BASED CHIRAL SEPARATION LIQUID CHROMATOGRAPHY STATIONARY PHASE

CROSS-REFERENCE TO RELATED APPLICATION

This is a divisional of application Ser. No. 08/402,663 filed Mar. 13, 1995, now U.S. Pat. No. 5,589,061.

BACKGROUND

As discussed in the *Kirk-Othmer Encyclopedia of Chemical Technology*, cellulose is a natural polymer of anhydro-D-glucose units having an empirical formula of $C_6H_{10}O_5$. Native cellulose can be dissolved and regenerated by a number of techniques to manufacture products such as rayon. Cellulose can be derivatized via the OH groups of its glucose units to form, for example, esters such as cellulose acetate, ethers such as methylcellulose and carbamates such as cellulose phenylcarbamate. Cellulose is composed of crystalline and amorphous regions. X-ray diffraction spectroscopy of the crystalline regions of cellulose reveals that cellulose has a different crystalline structure after it has been dissolved and then regenerated. The crystalline structure of native cellulose is classified as cellulose I. The crystalline structure of the different regenerated celluloses is classified as cellulose II, III or IV.

It is well known that enantiomers can be separated by liquid chromatography using an optically active stationary phase. Cellulose is a polymer of anhydro-D-glucose units. Native cellulose, derivatized native cellulose, regenerated cellulose and derivatized regenerated cellulose have all been used as the stationary phase in liquid chromatography to separate enantiomers.

The ability of any specific cellulose based liquid chromatographic stationary phase to separate any specific group of enantiomers depends primarily on the structure and chemistry of the enantiomers as they interact with the structure and chemistry of the cellulose. Thus, a specific cellulose based liquid chromatographic stationary phase will separate some enantiomers better than another cellulose based liquid chromatographic stationary phase. It is difficult to form some derivatives of cellulose without dissolving them. For example, it is difficult to form an aromatic acid ester or an aromatic carbamate of cellulose without dissolving it.

If the cellulose derivative is dissolved, then it must be precipitated before it can be used as a stationary phase for the liquid chromatographic separation of enantiomers. It is difficult to control the particle size and morphology of precipitated derivatized cellulose. The dissolved derivatized cellulose can alternatively be precipitated on a support, such as porous silica beads, but this is a difficult process and the resulting product is relatively expensive. Since liquid chromatography grade cellulose particles and fibers are commercially available which are relatively inexpensive, it would be an advance in the art of preparing derivatized cellulose for the separation of enantiomers if the cellulose could be derivatized without dissolving it.

SUMMARY OF THE INVENTION

A primary benefit of the instant invention is the preparation of an aromatic acid ester of cellulose or an aromatic carbamate of cellulose wherein the cellulose ester or cellulose carbamate is not dissolved. The instant invention in one embodiment is a method for preparing a cellulose ester liquid chromatography stationary phase by reacting cellulose with an aromatic acid halide in the presence of a base catalyst, the temperature being below the temperature at which the cellulose ester dissolves, the concentration of the base catalyst being below the concentration at which the cellulose ester dissolves and the reaction time being less than the reaction time at which the cellulose ester dissolves. The instant invention in another embodiment is a method for preparing a cellulose carbamate liquid chromatography stationary phase by reacting cellulose with an aromatic isocyanate in the presence of a base catalyst, the temperature being below the temperature at which the cellulose carbamate dissolves, the concentration of the base catalyst being below the concentration at which the cellulose carbamate dissolves and the reaction time being less than the reaction time at which the cellulose carbamate dissolves.

DETAILED DESCRIPTION OF THE INVENTION

Figure 1:
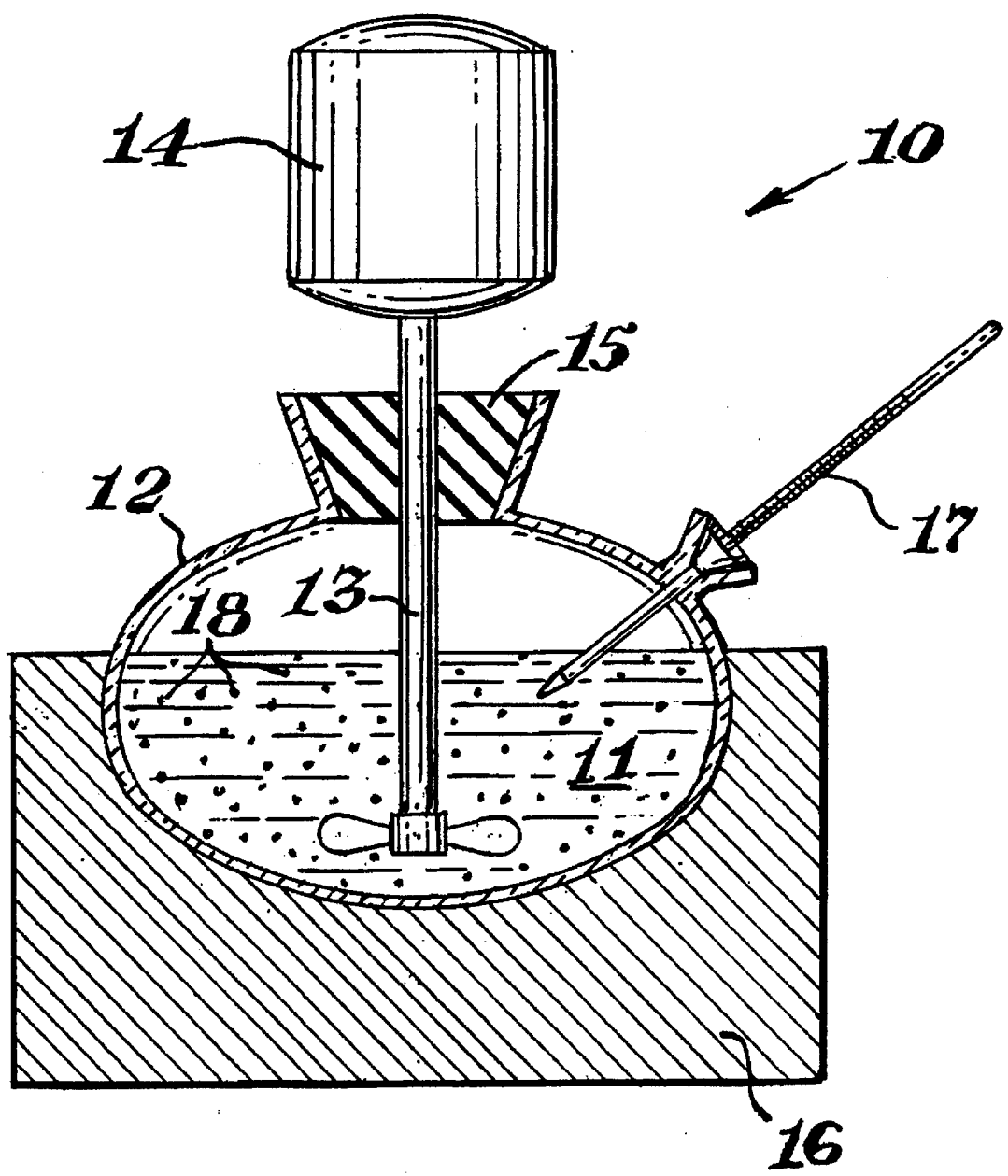
FIG. 1 shows an apparatus suitable for carrying out the process of the instant invention.

This invention is primarily directed towards the preparation of a liquid chromatographic stationary phase to be used for preparative or process scale separations of enantiomers. Therefore, it is preferable to begin with cellulose particles or fibers, native or regenerated, that are of a size suitable for preparative or process scale liquid chromatography. For example, Type 20 Sigmacell brand cellulose particles from Sigma Chemical Company, St. Louis, Mo. which are about twenty micrometers in diameter. Larger particles of cellulose can be used such as Type 50 Sigmacell brand cellulose particles from Sigma which are about fifty micrometers in diameter. Cellulose fibers can be used such as the Type 100 cellulose fibers from Sigma. On the other hand, cellulose particles can be used in this invention that are smaller than ordinarily used for preparative chromatography such as ten, five, three or even one micrometer diameter cellulose particles. Thus, the size of the cellulose particles or fibers is not critical in this invention.

In one embodiment of the invention the solid particles or fibers of cellulose are reacted with an aromatic acid halide, such as p-toluoyl chloride, in the presence of a base catalyst, such as pyridine to produce an aromatic acid ester of the cellulose. It is critical during the process of this embodiment of the instant invention that the cellulose or the cellulose ester not dissolve. It should be understood that some cellulose and the cellulose ester produced may dissolve in the process of this embodiment of the instant invention but this dissolved material can be separated from the remaining solid product. What is important is that a usable portion of solid product remain that has not been dissolved. Thus the term "dissolves" or "dissolve" here and in the claims means essentially completely dissolved.

The reaction between cellulose and the aromatic acid halide is carried out using the Schotten-Baumann reaction and thus requires a base catalyst such as aqueous sodium hydroxide or pyridine. Pyridine is preferred. Sufficient pyridine is preferably used to neutralize the acid produced by the reaction of the cellulose and the aromatic acid halide. However, if too much pyridine is used, then the cellulose ester will dissolve. The temperature of the reaction must be high enough so that the time needed to produce the cellulose ester is acceptable. However, if the reaction temperature is too high then the cellulose ester will dissolve. Similarly, the reaction time must be long enough to produce the cellulose ester but not so long that the cellulose ester dissolves.

When the reaction between the cellulose and the aromatic acid halide has been taken as far as desired, then it is preferable to wash the solid product with a solvent to wash away reaction biproducts such as pyridine hydrochloride. However, any solvent used to wash the cellulose ester must not dissolve the cellulose ester. Another problem that should be avoided during the wash step is precipitation of reaction biproducts such as pyridine hydrochloride onto the cellulose ester. Isopropanol is preferred as a wash solvent when the aromatic acid halide is p-toluoyl chloride and when the base catalyst is pyridine.

In another embodiment of the invention, similar in most respects to embodiment detailed above, the solid particles or fibers of cellulose are reacted with an aromatic isocyanate, such as 3,5-dimethyl phenyl isocyanate or p-chloro phenyl isocyanate, in the presence of a base catalyst, such as pyridine to produce an aromatic carbamate of the cellulose. It is critical during the process of this embodiment of the instant invention that the cellulose or the cellulose carbamate not dissolve. It should be understood that some cellulose and the cellulose carbamate produced may dissolve in the process of this embodiment of the instant invention but this dissolved material can be separated from the remaining solid product. What is important is that a usable portion of solid product remain that has not been dissolved. Thus the term "dissolves" or "dissolve" here and in the claims means essentially completely dissolved.

The reaction between cellulose and the aromatic isocyanate is carried out using a base catalyst such as pyridine. Pyridine is preferred in this embodiment of the instant invention. If too much pyridine is used, then the cellulose carbamate will dissolve. The temperature of the reaction must be high enough so that the time needed to produce the cellulose carbamate is acceptable. However, if the reaction temperature is too high then the cellulose carbamate will dissolve. Similarly, the reaction time must be long enough to produce the cellulose carbamate but not so long that the cellulose carbamate dissolves.

When the reaction between the cellulose and the aromatic isocyanate has been taken as far as desired, then it is preferable to wash the solid product with a solvent to wash away reaction biproducts such as ureas. However, any solvent used to wash the cellulose carbamate must not dissolve the cellulose carbamate. A three step wash is preferred when the aromatic isocyanate is 3,5-dimethyl phenyl isocyanate and when the base catalyst is pyridine: First, wash with hexane; then wash with an equal mixture of hexane and isopropanol; and then wash with isopropanol.

It has been found that it is preferable to dry the cellulose to remove water before reacting the cellulose with the aromatic isocyanate. If this is not done, then it is suspected that disubstituted ureas can form during the reaction which are difficult to remove by washing and which can interfere with the separation of some enantiomers. The disubstituted ureas apparently form by a reaction between the aromatic isocyanate and an amine, which amine forms by the reaction between the aromatic isocyanate and water. Similarly, it is preferable to blanket the reaction with dry nitrogen to keep water out during this step. The cellulose can be dried before the reaction step by heating the cellulose at forty degrees Centigrade in a vacuum oven for several hours to reduce the water content of the cellulose.

Referring now to FIG. 1, therein is shown an apparatus 10 suitable for carrying out the invention. The mixture of the aromatic acid halide (or aromatic isocyanate) and base 11 is contained in a flask 12. A stirrer 13, powered by a gear motor 14, is used to stir the mixture 11. The stirrer 13 is supported by bearing 15. A variable heater 16 is used to controllably heat the mixture 11. A thermometer 17 is used to monitor the temperature of the mixture 11. Particles of cellulose 18 are suspended in the mixture 11. A stream of dry nitrogen, not shown, is preferably used to blanket the reaction mixture during the reaction when an aromatic isocyanate is used.

EXAMPLE 1

2.8 grams of Type 20 Sigmacell brand cellulose particles form Sigma Chemical Company is reacted with 55 milliliters of p-toluoyl chloride and 10 milliliters of pyridine for nineteen hours at sixty degrees centigrade. After cooling to room temperature, the product of the reaction is washed five times with isopropanol. A portion of the washed product is then slurry packed into a 4.6 millimeter inside diameter, 25 centimeter long chromatography column.

1.6 milligrams of R/S methyl 2-(4-hydroxyphenoxy) propanoate is injected onto the column and developed with a mobile phase of 35:65 (volume basis) isopropanol/hexane at a flow rate of 70 microliters per minute. The R isomer begins to elute from the column at 285 minutes after the injection. The effluent from the column is then collected in a two milliliter vial which is replaced with a fresh vial periodically. The content of each vial is analyzed for the R and S isomer as indicated in Table I.

TABLE I

| COLLECTION TIME, MINUTES | R/S RATIO | % R/S |
| --- | --- | --- |
| 285–310 | 100/0 | 0.17/0 |
| 310–315 | 100/0 | 0.29/0 |
| 315–330 | 100/0 | 4.88/0 |
| 330–345 | 99.7/.3 | 24.7/0.1 |
| 345–360 | 97.3/2.7 | 30.3/0.8 |
| 360–375 | 82.1/17.9 | 20.9/4.5 |
| 375–393 | 40.4/59.6 | 12.1/17.6 |
| 393–405 | 17.0/83.0 | 3.5/16.8 |
| 405–420 | 9.5/90.5 | 2.0/19.2 |
| 420–435 | 5.2/94.8 | 0.8/15.3 |
| 435–450 | 2.5/97.5 | 0.3/11.1 |
| 450–465 | 1.2/98.8 | 0.1/7.4 |
| 465–480 | 0.6/99.4 | 0.03/4.6 |
| 480–495 | 0/100 | 0/2.6 | all values to the nearest tenth of a unit

The data in Table I indicates that collection between 345 and 375 minutes yields about 2.1 milliliters of solution containing 0.40 milligrams of 98+% pure R isomer.

EXAMPLE 2

4 grams of Type 20 Sigmacell brand cellulose particles form Sigma Chemical Company is heated at forty degrees centigrade in a vacuum oven to reduce its water content and then reacted under a blanket of dry nitrogen with 25 grams of 3,5-dimethyl phenyl isocyanate and 37.5 milliliters of pyridine for twenty one hours at fifty one degrees centigrade. After cooling to room temperature, the product of the reaction is washed several times with hexane, then a 1:1 mixture of hexane and isopropanol and then with isopropanol. A portion of the washed product is then slurry packed into a 50 millimeter long disposable pipet.

625 micrograms of R/S 2,2,2-trifluoro-1-(9-anthryl) ethanol is injected onto the pipet and developed with a mobile phase of 10:90 (volume basis) isopropanol/hexane at a flow rate of one half milliliter per minute. The R isomer begins to elute from the piper at 2 minutes after the injection. The effluent from the column is then collected in a two milliliter vial which is replaced with a fresh vial periodically. The content of each vial is analyzed for the R and S isomer as indicated in Table II.

TABLE II

| COLLECTION TIME, MINUTES | R/S RATIO | % R/S |
|---|---|---|
| 1-2 | 100/0 | 0.0/0.0 |
| 2-3 | 93.4/6.6 | 0.5/0.0 |
| 3-4 | 98.4/1.6 | 8.1/0.1 |
| 4-5 | 96.7/3.3 | 43.0/1.4 |
| 5-6 | 86.7/13.3 | 40.6/6.1 |
| 6-7 | 23.7/76.3 | 7.0/22.0 |
| 7-8 | 2.0/98.0 | 0.7/33.5 |
| 8-9 | 0.6/99.4 | 0.1/22.0 |
| 9-10 | 0.4/99.6 | 0.0/9.6 |
| 10-11 | 0.7/99.3 | 0.0/3.2 |
| 11-12 | 0.6/98.4 | 0.0/1.1 |
| 12-13 | 0/100 | 0.0/0.4 |
| 13-14 | 0/100 | 0.0/0.2 | all values to the nearest tenth of a unit

The data in Table II indicates that collection between 4 and 5 minutes yields about 0.5 milliliters of solution containing 134 micrograms of 97% pure R isomer.

What is claimed is:

1. A process for preparing a cellulose carbamate liquid chromatographic stationary phase, comprising the step of: reacting solid cellulose with an aromatic isocyanate in the presence of a base catalyst, the temperature being below the temperature at which the cellulose carbamate dissolves, the concentration of the base catalyst being below the concentration at which the cellulose carbamate dissolves, the reaction time being less than the reaction time at which the cellulose carbamate dissolves.

2. The process of claim 1, further comprising the step of washing the cellulose ester with a solvent which does not dissolve the cellulose carbamate.

3. The process of claim 1, wherein the aromatic isocyanate is 3,5-dimethyl phenyl isocyanate.

4. The process of claim 3, further comprising the step of washing the cellulose ester with a solvent which does not dissolve the cellulose carbamate.

5. The process of claim 4, wherein the solvent is hexane and then a mixture of hexane and isopropanol and then isopropanol.

6. The process of claim 5, wherein the base catalyst is pyridine.

7. The process of claim 6, further comprising the step of drying the solid cellulose to reduce its water content.

8. The process of claim 4, wherein the base catalyst is pyridine.

9. The process of claim 8, further comprising the step of drying the solid cellulose to reduce its water content.

10. The process of claim 3, wherein the base catalyst is pyridine.

11. The process of claim 10, further comprising the step of drying the solid cellulose to reduce its water content.

12. The process of claim 1, wherein the aromatic isocyanate is p-chloro phenyl isocyanate.

13. The process of claim 1, wherein the base catalyst is pyridine.

14. The process of claim 13, further comprising the step of drying the solid cellulose to reduce its water content.

15. The process of claim 1, further comprising the step of drying the solid cellulose to reduce its water content.

* * * * *